US010353037B2

(12) United States Patent
Franger et al.

(10) Patent No.: US 10,353,037 B2
(45) Date of Patent: Jul. 16, 2019

(54) CONTROL OF A MAGNETIC RESONANCE FACILITY BY AN EXTERNAL CONTROL DEVICE

(71) Applicant: Siemens Healthcare GmbH, Erlangen (DE)

(72) Inventors: Dirk Franger, Erlangen (DE); Rainer Schneider, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 107 days.

(21) Appl. No.: 15/410,119

(22) Filed: Jan. 19, 2017

(65) Prior Publication Data
US 2017/0205484 A1 Jul. 20, 2017

(30) Foreign Application Priority Data
Jan. 19, 2016 (DE) .................... 10 2016 200 631

(51) Int. Cl.
*G01R 33/28* (2006.01)
*G01R 33/54* (2006.01)
*A61B 5/055* (2006.01)
*A61B 5/00* (2006.01)
*A61B 6/00* (2006.01)
*G05B 19/042* (2006.01)

(52) U.S. Cl.
CPC .......... *G01R 33/546* (2013.01); *A61B 5/0046* (2013.01); *A61B 5/055* (2013.01); *A61B 6/548* (2013.01); *G01R 33/283* (2013.01); *G01R 33/543* (2013.01); *G05B 19/042* (2013.01)

(58) Field of Classification Search
CPC .. G01R 33/546; G01R 33/283; G01R 33/543; A61B 5/0046; A61B 5/055; A61B 6/548; G05B 19/042
USPC ........................................................ 324/309
See application file for complete search history.

(56) References Cited

U.S. PATENT DOCUMENTS

| 6,198,285 | B1 | 3/2001 | Kormos et al. |
| 7,263,710 | B1 | 8/2007 | Hummel, Jr. et al. |
| 8,094,909 | B2 | 1/2012 | Maier et al. |
| 9,953,181 | B2 * | 4/2018 | Dunaway ............... G06F 21/00 |
| 2011/0013220 | A1 | 1/2011 | Sabol et al. |
| 2013/0088452 | A1 | 4/2013 | Glaser-Seidnitzer et al. |
| 2013/0321284 | A1 | 12/2013 | Bello et al. |
| 2014/0058383 | A1 | 2/2014 | Hoyme et al. |
| 2015/0366517 | A1 | 12/2015 | Hoelscher et al. |
| 2016/0054414 | A1 | 2/2016 | Haider et al. |

FOREIGN PATENT DOCUMENTS

| DE | 100 65 558 A1 | 7/2001 | |
| DE | 10 2011 083 957 A1 | 4/2013 | |
| DE | 10 2013 105 043 A1 | 12/2013 | |
| DE | 10 2014 216 669 A1 | 2/2016 | |
| JP | 2008097187 A * | 4/2008 | |
| WO | WO 2008050571 A1 * | 5/2008 | ............. A61B 5/055 |

* cited by examiner

Primary Examiner — Susan S Lee
(74) Attorney, Agent, or Firm — Schiff Hardin LLP

(57) ABSTRACT

A magnetic resonance facility is operated by an external control device. The magnetic resonance facility includes an interface for communicating with the external control device and establishes a communications link between the external control device and the magnetic resonance facility via the interface, acquire an instruction from the external control device via the interface, and carries out the instruction on the magnetic resonance facility.

16 Claims, 4 Drawing Sheets

FIG 3

| | Copy | Paste | | | | | | | | |
|---|---|---|---|---|---|---|---|---|---|---|
| Guidance | | | | | | | | | | |
| Parameters | | | | | | | | | | |
| Queue | | | | | | | | | | P |
| GSP | | Slices ~51 | | P | | FoV read ~53 | | P | | |
| Series Label | | Slices Thickness ~52 | | P | | FoV phase ~54 | | P | | |
| Auto load | | | | P | | | | P | | |
| AutoCoverage | | | | P | | | | P | | |
| AutoTiming | | | | P | | TR ~55 | | P | | |
| Interactive Realtime | | | | P | | Concatenations ~56 | | P | | |
| Remote Control | | | | P | | | | P | | |
| | | | | | | Advanced mode | | | | |
| | | | | | | Close | | | | |

CONTROL OF A MAGNETIC RESONANCE FACILITY BY AN EXTERNAL CONTROL DEVICE

BACKGROUND OF THE INVENTION

Field of the Invention

The present invention relates to the control of a magnetic resonance facility with the use of an external control device.

Description of the Prior Art

A magnetic resonance facility makes it possible to constantly generate images of a specific volume segment of a patient. As a result, the operator or therapist can continually monitor the patient during an operation or treatment on the basis of these images. However, to control the magnetic resonance facility, in order for example to change the manner in which the images are acquired, or the volume segment to be acquired, it is necessary according to the prior art for corresponding instructions to be entered laboriously via an input console of the magnetic resonance facility, and this console is not located in the vicinity of the patient.

SUMMARY OF THE INVENTION

An object of the present invention is to address the problem of improving the control of a magnetic resonance facility such that this control can ensue at any point (for example, even in the vicinity of the patient).

In accordance with the present invention, a method for operating a magnetic resonance facility using an external control device is provided. Here the magnetic resonance facility includes an interface, in order to implement a communication with the external control device via this interface. The magnetic resonance facility executes the following steps.

A communications link is established between the external control device and the magnetic resonance facility via the interface.

An instruction is acquired from the external control device via the interface and the communications link.

The instruction is carried out by the magnetic resonance facility.

An external control device as used herein means a control device (for example, a mobile device, such as a tablet, a PC, a smartphone or any device that is suitable for communication via a standardized internet protocol), that is spatially removed from the magnetic resonance facility. The interface can be a wireless or wired interface. In particular, the interface is standardized and uses for example a REST ("Representational State Transfer")-based HTTP protocol, which allows the external control device to use any technology that supports TCP/IP and HTTP. That is, LANs, WANs and all kinds of internet links are supported as the communications link.

The instruction with which the external control device controls the magnetic resonance facility can be what is known as a write or change instruction, with which a sequence in the magnetic resonance facility can be written or changed, for example. It is also possible, however, for the instruction to involve (only) what is known as Read access to data or information items relating to the magnetic resonance facility, in order to be able to display specific image data on the external control device, for example.

The method according to the invention allows the use of an external control device in any location such that the magnetic resonance facility can be controlled from this random location (in the direct vicinity of the patient, for example) via said external control device.

According to a preferred embodiment of the invention, authorization data for the external control device are acquired by the magnetic resonance facility in the context of the establishment of the establishment of the communications link. The authorization data include a license that contains information regarding which services or instructions can be carried out by the magnetic resonance facility via the external control device. Each instruction acquired is then carried out by the magnetic resonance facility as a function of an authorization, which is defined by this license. Here, the license is preferably an autonomous ("self-contained") license, which fully defines the respective authorization without the magnetic resonance facility requiring further information sources to acquire the authorization (apart from the license). The license is generated individually for each external control device or user of each external control device.

Through this authorization according to the invention, it is possible to specify very precisely which service or which instruction (or operation or method) in the magnetic resonance facility may be carried out by use of the respective external control device.

A number of types of authorization can exist, and the authorization defined by the license includes one or more types of authorization. Each instruction in the magnetic resonance facility and/or each service in the magnetic resonance facility is assigned to one of these types of authorization. The instruction acquired is now carried out by the magnetic resonance facility if the authorization includes that type of authorization that is assigned to the instruction and/or if the authorization includes that type of authorization that is assigned to the service that provides the instruction.

Through the embodiment described above, the method according to the invention allows a very precise gradation of authorizations for operations and methods (instructions) in the magnetic resonance facility on the part of the respective external control device. As a result, it is possible to comply with legal and commercial conditions.

Through the authorization described above, only authorized users can connect to the magnetic resonance facility via the external control device, a specific (that is, user-specific) license, which is assigned to a specific authorization is used.

A communications link can be established with the same magnetic resonance facility by a number of external control devices (in each case). Therefore, a plurality of communications links can exist at the same time between the same magnetic resonance facility and various external control devices.

This embodiment according to the invention makes it possible for a plurality of external control devices to access the same magnetic resonance facility at the same time. Likewise, a number of processes or tasks of the same external control device can access the same magnetic resonance facility at the same time. For example, image data can be acquired with an external control device while at the same time parameters in a sequence of the same magnetic resonance facility are changed by a different external control device.

Via the interface, an information service can be provided, which provides the external control device with one or a number of the following operations or instructions:

Acquiring a list of sequences that can be carried out by the magnetic resonance facility. Via this instruction, the external control device can acquire a list of sequences available to the magnetic resonance facility, the external control device being able to open and start each of these sequences.

Acquiring a current status of a specific or selected sequence. The following status levels exist for a sequence:
current:
The sequence is currently running on the magnetic resonance facility.
open:
The sequence is open so that, for example, parameters in the sequence can be changed.
stopped:
The sequence has been stopped and can be continued.

Acquiring the remaining scanning time in a sequence that is currently running on the magnetic resonance facility. This information is of interest in particular for non-interactive sequences, which do not require any action by a user (such as, for example, a table movement or a pause for breath), since the remaining scanning time then shows precisely the time interval that the sequence currently running still requires until it comes to an end.

According to a further embodiment as per the invention, a control service is provided by the magnetic resonance facility via the interface, which service provides one or more of the following operations or methods (instructions) to the external control device:

Opening a specific sequence. The opening of the sequence is a prerequisite for changing the parameters in this sequence.

Closing a specific sequence. The closing of an open sequence includes in particular retaining parameter changes previously carried out or rejecting parameter changes that were previously carried out with respect to the sequence.

Starting the currently open sequence. As a result of this instruction, the status of the sequence changes from open to running, and MR data is acquired by means of the magnetic resonance facility depending on the sequence.

Aborting the sequence that is currently running. As a result of this instruction, the sequence is stopped and the protocol is automatically closed. The sequence cannot be continued, only started afresh.

In order to carry out one of the aforementioned instructions from the control service for a specific sequence, the specific sequence in particular is selected beforehand from the list of available sequences that is provided by the information service.

Furthermore, a change service can be provided by the magnetic resonance facility via the interface, which service provides the external control device with one or a plurality of the following instructions:

Changing one or a plurality of parameters for a specific sequence. This also includes changing the parameters in a sequence that is currently running.

Stopping the sequence that is currently running. Stopping or pausing a sequence means that the sequence does not currently acquire any MR data such that the magnetic resonance facility is silent. Unlike an aborted sequence, a stopped sequence can be continued.

Continuing the sequence that is currently stopped. The previously stopped sequence is continued such that the sequence acquires MR data again.

The change service according to the invention allows the external control device to change the scanning properties of sequence by changing the parameters of a sequence accordingly in order in this way to influence and/or change the result (in particular the MR images generated using the MR data acquired by the sequence). Here, the parameters for the sequence that is currently running can be changed by the external control device, it being possible to limit the number of parameters that are to be changed by the external control device, as set out hereinafter.

Furthermore, a patient data service can be provided by the magnetic resonance facility via the interface, via which service the external control device can acquire one or a plurality of the following information items:
The patient's name.
The patient's age.
The patient's body length.
The patient's weight.

Using this patient data, the sequence, for example, in which the MR images of the patient are generated can be adjusted to the patient. Access to this patient data via the external control device is advantageously restricted only to users with a corresponding authorization.

According to a further embodiment of the invention, an interactive service can be provided by the magnetic resonance facility via the interface, via which service a report or notification issued by the magnetic resonance facility is forwarded to the external control device.

Via this interactive service according to the invention, notifications and/or reports from the magnetic resonance facility that provide information on an action of the magnetic resonance facility, which is some cases requires dialogue input by a user, can be forwarded to the external control device. This can include for example a notification or a report or information about a pending table movement, about an automatic adjustment of the protocol that is currently open, or about a warning regarding a nerve-stimulation (for example due to the rapidly changing magnetic gradient fields) or the administration of a contrast agent to the patient.

If the notification or report requires a confirmation so that the currently stopped sequence in the magnetic resonance facility is continued, this confirmation can be forwarded to the magnetic resonance facility by the external control device.

For example, the control device can periodically query whether a confirmation is required. If this is the case, the external control device can display on its display panel the report acquired by the magnetic resonance facility via the interactive service in order to then acquire a corresponding user input (for example, a confirmation or abort instruction) and forward it to the magnetic resonance facility.

The interactive service is in particular designed generically. The external control device therefore has no knowledge of the semantics of the report acquired by the interactive service but shows on its display panel only the report that has been transmitted and the options for responding (a confirmation and where necessary an abort instruction). The response inputted by the user of the external control device is then transmitted to the magnetic resonance facility.

If the report is transmitted before the start of the respective sequence, an abort instruction leads to the sequence not being started. A response (including an abort response to the report) will not necessarily entail an effect on the running or further running of the sequence. For example, an abort response may lead only to a movement of the table not being carried out.

According to a further embodiment of the invention, a parameter service is provided by the magnetic resonance facility via the interface, through which service an interface is provided to the external control device in order to acquire, via this interface parameter information, relating to parameters for sequences in the magnetic resonance facility.

It is possible accordingly, via the interface provided by the parameter service, to provide not only parameters and subsets of parameters, but also information items about the parameters.

For example, a subset of those parameters that may be changed by the external control device with respect to the specific sequence can be provided by the magnetic resonance facility to the external control device via this interface, regarding the specific sequence.

While only those parameters that may be changed can be provided to the external control device in the form of the subset, it is advantageously ensured that the external control device in this embodiment does not change other parameters that should not be changed by the average user with respect to the specific sequence. This subset of the modifiable parameters usually differs between the various sequences since each sequence has its individual properties and requests.

The parameter information can include one or a plurality of information items from an information set, wherein the information set itself includes the following information:

Information on the availability and modifiability of the parameter. This information states whether the respective parameter is available for the corresponding sequence and whether the respective parameter can be modified for the corresponding sequence.

A designation of the parameter. An internationally usual designation is advantageously used here.

A type and a unit for the parameter.

Valid values for the parameter. If this parameter value is an element in a finite list (for example "yes", "no"), this finite list of the valid parameter values is provided to the external control device.

Information on a selectable value range for the parameter. This information can include, for example, a minimum value and a maximum value, between which is a valid value for the parameter.

A detailed description of the parameter. This description provides a precise definition of the parameter.

A clear identification of the parameter. Through this identification, the parameter can be clearly referenced in an instruction sent by the external control device to the magnetic resonance facility.

The interface in the parameter service also advantageously provides the option of generating a previously described subset of the parameters and of changing said subset. In other words, for a specific sequence it is possible to generate or change a subset that includes those parameters of the sequence that can be changed (later) by the external control device with respect to said sequence.

This configuration of the subsets of those parameters that can be changed by the external control device with respect to a specific sequence can for example be provided only if the external control device or to be more precise, the user of the external control device, has a corresponding authorization. This changing or generating of a subset can also include generating and changing the previously described parameter information for each parameter in the respective subset.

Normally, generating and changing the subsets of those parameters that can be changed by the external control device with respect to a specific sequence are the responsibility of a specialist, such that it is also sufficient if this generating and changing process is only possible directly on the magnetic resonance facility (and not via an external control device).

Furthermore, each parameter in any sequence of the magnetic resonance facility can be changed via the external control device, depending on the authorization data (that is, depending on the authorization).

The interface that is provided by the parameter service according to the invention is advantageously a generic interface. As a result, the external control device can access any parameter in a sequence in a uniform manner, without having to know any inherent properties of the parameter. As a result, advantageously the subset of those parameters that may be changed by the external control device with respect to a specific sequence can likewise be extended in any manner without a change of the software in the external control device being required. In other words, it is also possible to add to this subset a parameter that is hitherto not been known to the external control device. Even the number of parameters within this subset is freely selectable without any changes to the software in the external control device being necessary. Due to the generic nature of the interface, the external control device does not require any kind of semantic prior knowledge of the number and the type of parameters nor any internal prior knowledge of the meaning and designation of a parameter. Any information required to carry out the instructions described in advance is provided to the external control device via the generic interface.

In the context of the present invention a magnetic resonance facility is likewise provided. Here the magnetic resonance facility includes a scanner having a basic field magnet, a gradient field system, at least one RF antenna, an interface for communicating with an external control device and a control device, to activate the gradient field system and the at least one RF antenna, for receiving measurement signals received by the RF antenna/antennas, and for evaluating the measurement signals. The magnetic resonance facility is designed so as to acquire an instruction from the external control device via the interface and carry out this instruction.

The advantages of the magnetic resonance facility according to the invention essentially correspond to the advantages of the method according to the invention, which have been described above in detail.

The present invention also encompasses a non-transitory, computer-readable data storage medium encoded with programming instructions (program code) that, when the storage medium is loaded into a computer or computer system of a magnetic resonance facility, cause the computer or computer system to operate the magnetic resonance facility to implement any or all embodiments of the method according to the invention as described above. The computer may require components such as libraries and auxiliary functions, in order to implement the respective embodiments of the method. The program code can be a source code (C++for example), which still has to be compiled (translated) and linked up or just has to be interpreted, or an executable software code that only remains to be loaded into the corresponding computation unit or control device to run the program.

The electronically readable data-carrier can be a DVD, a magnetic tape, a hard disk, or a USB stick, on which electronically readable control data, in particular software (see above), is stored.

Finally, the present invention encompasses a system that includes a magnetic resonance facility according to the invention and an external control device. Here the control device itself includes a control, an interface for communicating with a magnetic resonance facility and a display unit. The control device is designed to establish a communications link with the magnetic resonance facility via the interface and to send an instruction to the magnetic resonance facility via the interface.

The advantages of the system according to the invention essentially correspond to the advantages of the method according to the invention, as described in detail above.

The present invention has the following advantages:

The invention allows remote control of an entire MRI examination via the external control device.

All the relevant information on the currently running sequence or on an open sequence, the list of available sequences, and the patient data can be displayed on the external control device.

No direct dialogue with the magnetic resonance facility is necessary. This means that the user (the operator or therapist, for example) can carry out the entire treatment including all the MR imaging via the external control device, without leaving the patient alone or asking for help from another person who is in direct control of the magnetic resonance facility.

A number of external control devices can be connected to the magnetic resonance facility at the same time.

Communication between the external control device and the magnetic resonance facility can be based on a standardized protocol which makes it easier to integrate further services.

With the external control device alone, a specialist is in a position to configure the parameters available to an external control device for each sequence, depending on the type of sequence and depending on the context and the application, in which the sequence is used.

The software according to the invention run in an external control device does not have to be altered, due to implementation rules for example. Instead, it is sufficient to change parameter information items on the magnetic resonance facility itself and to provide them to the external control device via the corresponding interface.

The present invention allows the following actions via the external control device:

Properties of the currently running MR sequence (for example, slice position, slice orientation) can be changed.

The currently running MR sequence can be stopped and continued.

A list of the MR sequences available from the magnetic resonance facility can be opened, it being possible to change and start the open sequence.

The currently running MR sequence can be aborted.

The name of the MR sequence that is currently open or currently running can be displayed.

The remaining scanning time for a currently running non-interactive MR sequence can be displayed.

The properties of an open MR sequence can be edited while a different non-interactive MR sequence is running.

Reports from the magnetic resonance facility, for example, a warning of a table movement or of an automatic adjustment of the MR sequence can be displayed and confirmed.

BRIEF DESCRIPTION OF THE DRAWINGS

FIG. 3 shows a menu for setting the parameters that are modifiable with respect to a sequence according to the present invention.

DESCRIPTION OF THE PREFERRED EMBODIMENTS

Figure 1:
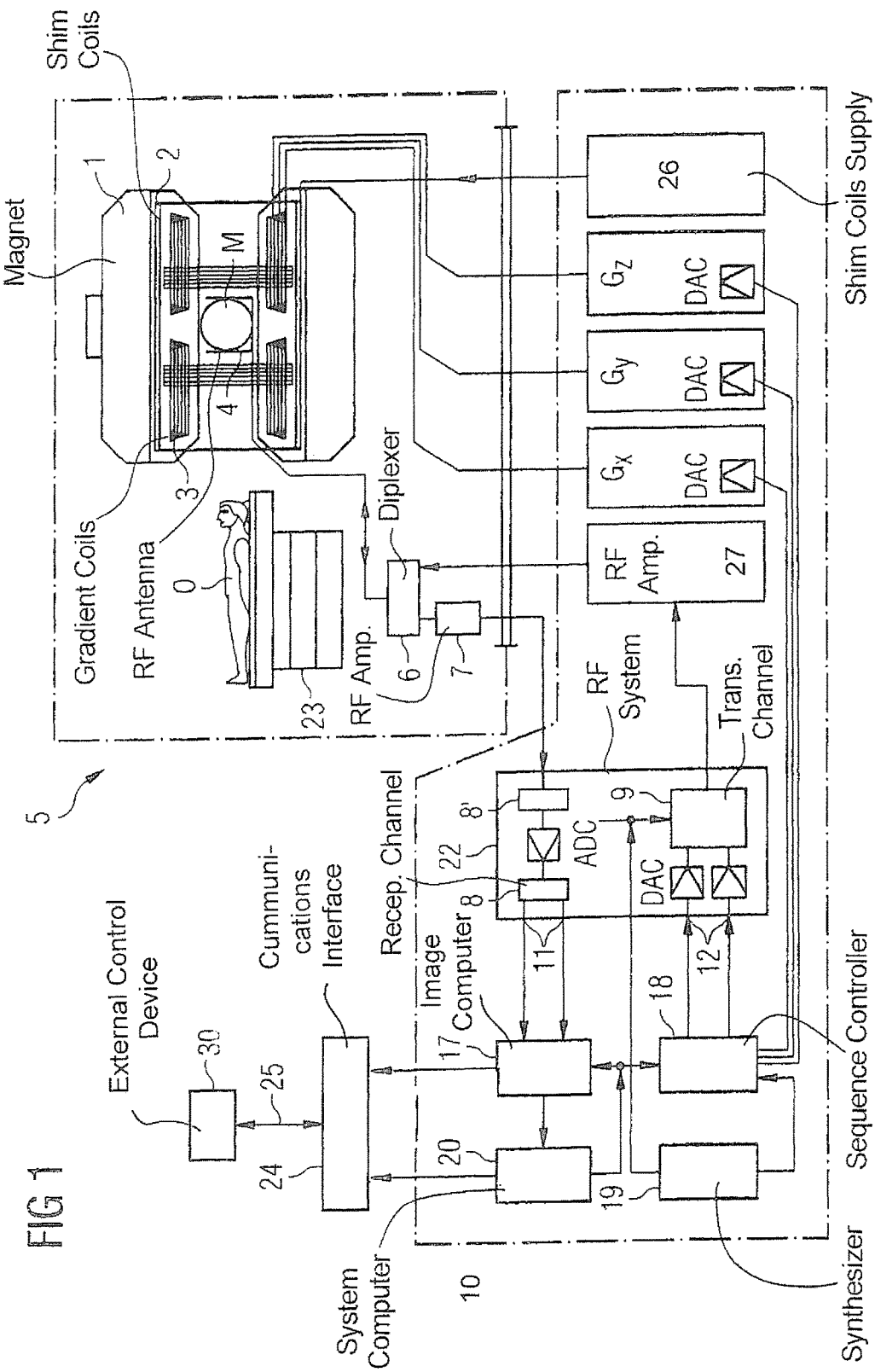
FIG. 1 is a block diagram of a magnetic resonance facility according to the invention with a communications link with an external control device.

FIG. 1 shows a magnetic resonance facility 5 according to the invention (a magnetic resonance imaging or magnetic resonance tomography device) in a communications link 25 with an external control device 30. Here, a basic field magnet 1 in the magnetic resonance facility 5 generates a chronologically constant strong magnetic field to polarize or align the nuclear spins in an examination region of an object O, such as a part of a human body that is to be examined, lying on a table 23 in the magnetic resonance facility 5. The high homogeneity of the basic magnetic field that is required for the nuclear spin resonance measurement is defined in a typically spherical measurement volume M defined, in which the volume segment of the human body that is to be examined is arranged. To support the homogeneity requirements and in particular to eliminate chronologically invariable influences, "shim plates" of ferromagnetic material are applied. Chronologically variable influences are eliminated by shim coils 2 fed by a shim coils supply 26.

In the basic field magnet 1, a cylindrical gradient field system or gradient field system 3 composed of three windings is used. Each partial winding is supplied by an amplifier with current to generate a linear (also chronologically modifiable) gradient field in the respective direction of the Cartesian coordinate system. The first winding in the gradient field system 3 generates a gradient $G_x$ in the x-direction, the second winding generates a gradient $G_y$ in the y-direction and the third winding generates a gradient $G_z$ in the z-direction. The amplifier includes a digital-analog converter, which is activated by a sequence control 18 to generate gradient pulses at the correct time.

Within the gradient field system 3 is one (or a number of) radio-frequency antennas 4, which convert the radio-frequency pulses emitted by a radio-frequency power amplifier 27 into an alternating magnetic field to excite the nuclei and thereby deflect the nuclear spins of the object O that is to be examined or of the region of the object O that is to be examined, from the alignment produced by the basic magnetic field. Each radio-frequency antenna 4 has one or more RF transmission coils and one or more RF receiving coils in the form of an annular, preferably linear or matrix-shaped arrangement, of component coils. The RF receiving coils in the respective radio-frequency antenna 4 also convert the alternating field emanating from the precessing nuclear spins, usually nuclear spin echo signals excited by a pulse sequence from one or more radio-frequency pulses and one or more gradient pulses, into a voltage (measurement signal), which is supplied to a radio-frequency receiving channel 8 of a radio-frequency system 22 via an amplifier 7. The radio-frequency system 22, which is part of a control computer 10 of the magnetic resonance facility 5, further includes a transmission channel 9, in which the radio-frequency pulses to excite the nuclear magnetic resonance are generated. Here the respective radio-frequency pulses are represented digitally as a succession of complex numbers, based on a pulse sequence that is preset in the facility's computer 20 in the sequence control 18. This sequence of numbers is supplied in each case as a real part and as an imaginary part via respective inputs 12 of a digital-analog converter in the radio-frequency system 22, and from this to a transmission channel 9. In the transmission channel 9, the pulse sequences are modulated onto a radio-frequency carrier signal, whose basic frequency corresponds to the resonant frequency of the nuclear spins in the measured volume.

Switching from transmitting to receiving mode is achieved via a duplexer 6. The RF transmission coils in the radio-frequency antenna(s) 4 radiate the radio-frequency pulses to excite the nuclear spins in the measured volume M and the resulting echo signals are sampled via the RF receiving coil(s). The nuclear resonance signals acquired accordingly are demodulated to an intermediate frequency in the receiving channel 8' (first demodulator) of the radio-frequency system 22 in a phase-sensitive manner, digitized in the analog-digital converter (ADC) and emitted via the output 11. This signal is demodulated again to a frequency of zero. The demodulation to a frequency of zero and the splitting into the real and imaginary parts takes places in a second demodulator 8 after the digitization in the digital domain. In an image processor 17, an MR image is reconstructed from the measured data thus acquired via an output 11. The management of the measured data, of the image data and of the control program is achieved via the facility's computer 20. On the basis of a target set using control programs, the sequence control 18 monitors the generation of the respective desired pulse sequences and the respective sampling of k-space. In particular, the sequence control 18 monitors the timing with which the gradients are switched, the transmission of the radio-frequency pulses with a defined phase amplitude, and also the reception of the magnetic resonance signals. The time base for the radio-frequency system 22 and sequence control 18 is provided by a synthesizer 19. The selection of corresponding sequences or control programs to generate an MR image can be carried out, for example via the external control device 30, which is linked via a standardized communications interface 24 to the magnetic resonance facility 5 according to the invention.

Figure 2:
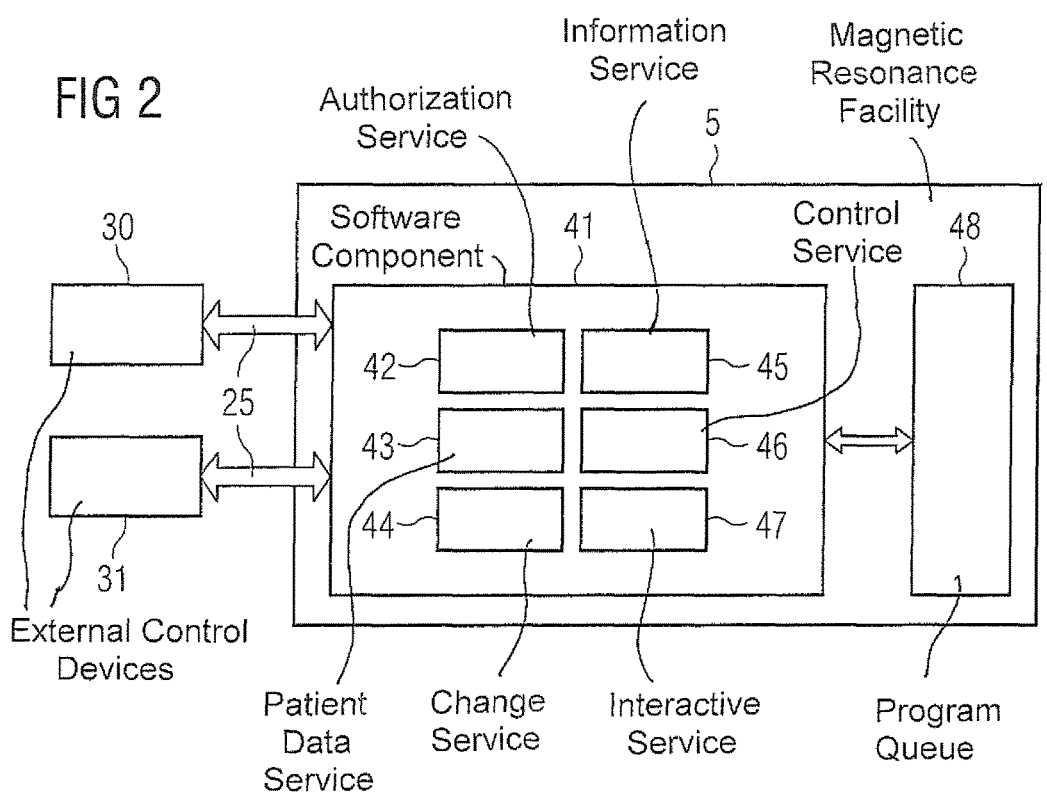
FIG. 2 shows a software component according to the invention of the magnetic resonance facility in combination with external control devices.

FIG. 2 essentially shows a software component 41 of the magnetic resonance facility 5 in combination with two external control devices 30, 31. The software component 41, which runs in the computation system of the magnetic resonance facility 5, includes an authorization service 42, a patient data service 43, a change service 44, an information service 45, a control service 46 and an interactive service 47. The software component 41 is connected to a program queue 48. The two external control devices 30, 31 each have a communications technology connection to the magnetic resonance facility 5 via a communications link 25.

Via this communications link 25, the respective external control device 30, 31 can issue the magnetic resonance facility 5 with a command that is provided by one of the services 42-47. Depending on the authorization of the user of the external control device 30, 31, this instruction is then carried out by the respective service 42-47 by the magnetic resonance facility 5.

FIG. 3 shows a menu, for defining the parameters that may be modified for a specific sequence by the external control device. In this menu, "Slices" 51 states the number of slices to be acquired, "Slice thickness" 52 states the respective slice thickness, "FoV read" 53 states the length of the layer in the read direction, "FoV phase" 54 states the length of the layer in the phase encoding direction, "TR" 55 states the repetition time and "Concatenation" 56 states the number of repeats. There is normally no access to this menu via the external control device.

Figure 4:
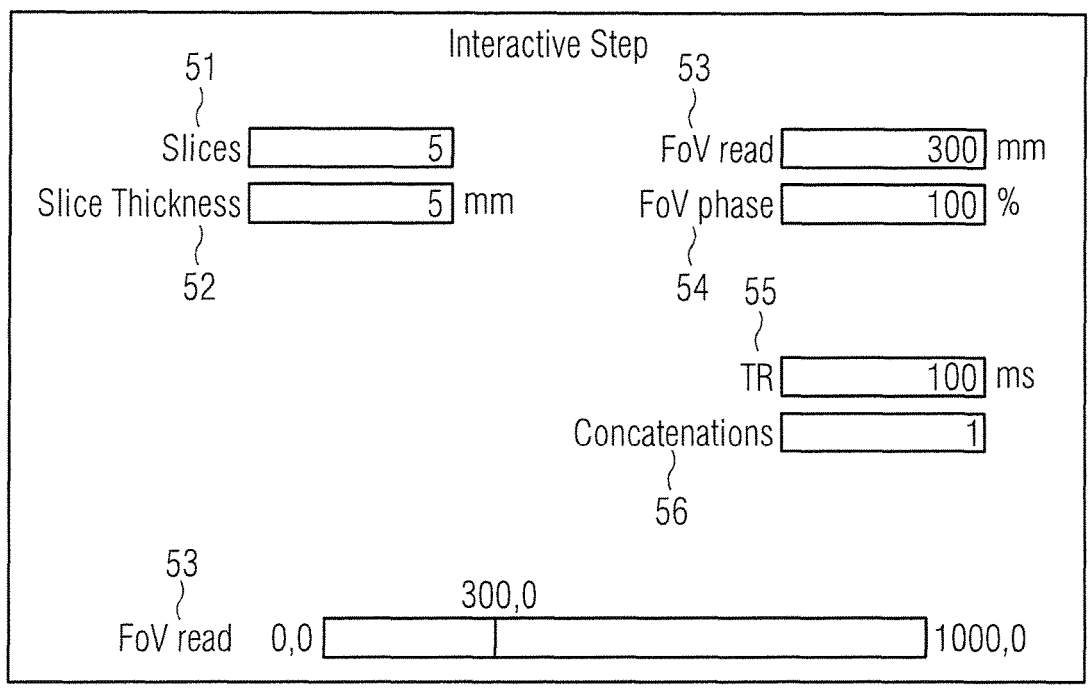
FIG. 4 shows an example of a configuration of the modifiable parameters according to FIG. 3.

FIG. 4 shows, as an example, the respective parameter values for the parameters 51-56 shown in FIG. 3.

This input mask shown in FIG. 4 is used in particular for inputting the parameter values via the external control device 30, 31.

A typical workflow according to the invention is set out below.
1. An external control device logs onto the magnetic resonance facility with a valid license, which is evaluated by the authorization service. The authorization of the external control device, or more precisely of the user of the external control device, is acquired from the authorization service by the license. The following steps are carried out only if the authorization is sufficiently high for the corresponding action or operation.
2. The external control device acquires the list of available sequences of the magnetic resonance facility by means of the information service.
3. With the use of the control service, the external control device opens an interactive sequence previously selected from the aforementioned list. The external control device subsequently modifies various parameters in this sequence via the change service and starts the sequence via the control service. In an interactive sequence that is running, the parameters can be changed, as a result of which a change in real time is made possible. A sequence that is running can be stopped by the change service (that is, the sequence is paused and the magnetic resonance facility does not acquire any MR data) and continued later.
4. After a certain time, the external control device aborts the sequence that is currently running by means of the control service, opens a non-interactive sequence, modifies some parameters in this sequence and starts this sequence. In this embodiment, the protocol of a non-interactive sequence is immediately closed when the sequence is started.
5. While the non-interactive sequence is running, the external control device opens a different sequence and modifies the parameters thereof. In order to start the sequence that has been opened, the sequence that is currently running either has to be aborted or it is necessary to wait until the sequence that is running has been terminated
6. The external control device logs off from the magnetic resonance facility.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for operating a magnetic resonance facility from an external control device comprising:
providing the magnetic resonance facility, that is an operational state, with an interface for communication with the external control device;
establishing a communications link between the external control device and the magnetic resonance facility via the interface, with acquisition of authorization data from the external control device, the authorization data comprising a license that states which services or instructions in the magnetic resonance facility can be carried out by the external control device, and said authorization data changing said operational state to a license-defined state that permits only said services or instructions stated in said license to be executed by said magnetic resonance facility;

at the magnetic resonance facility, acquiring an instruction from the external control device via the interface;

carrying out the instruction at the magnetic resonance facility in order to operate said magnetic resonance facility to acquire magnetic resonance data from a subject only when said instruction is permitted by the license comprised in said authorization data, with the acquired magnetic resonance data thereby being defined by said instruction; and reconstructing an image of the subject from the acquired magnetic resonance data that were defined by said instruction, and making the reconstructed image available in electronic form, as a data file.

2. The method as claimed in claim 1, wherein a plurality of types of authorization exist, and including at least one of the types of authorization in the authorization data;

assigning each instruction of the magnetic resonance facility and/or each service of the magnetic resonance facility to one of the types of authorization; and carrying out the instruction at the magnetic resonance facility that has been acquired only if the authorization has the type of authorization that is assigned to the instruction and/or that is assigned to a service that is assigned to the instruction.

3. The method as claimed in claim 1, comprising:

at the magnetic resonance facility, establishing a plurality of communications links to a plurality of external control devices, so at least a subset comprising more than one of said plurality of communications links between an external control device and the magnetic resonance facility is available at the same time.

4. The method as claimed in claim 1, comprising:

providing an information service by the magnetic resonance facility via the interface, and with said information service carrying out at least one of the following instructions:

acquiring a list of sequences that are available to the magnetic resonance facility, acquiring a current status of a specific sequence, and acquiring a remaining scanning time for a sequence that is currently running on the magnetic resonance facility.

5. The method as claimed in claim 1, comprising:

providing a control service at the magnetic resonance facility via the interface and with said control service carrying out at least one of the following:

opening a specific sequence, closing a specific sequence, starting a sequence that has been opened, and aborting a sequence that has been started.

6. The method as claimed in claim 1, comprising:

providing a patient data service at the magnetic resonance facility via the interface, and with said patient data service acquiring at least one of the following information items:

a patient's name, a patient's age, a patient's body length, and a patient's weight.

7. The method as claimed in claim 1, comprising:

providing an interactive service at the magnetic resonance facility via the interface, and wish said interactive service forwarding, to the external control device, a report issued by the magnetic resonance facility.

8. The method as claimed in claim 7, wherein the report requires a confirmation so that a sequence that is currently running in the magnetic resonance facility is continued, and comprising:

acquiring said confirmation by the external control device.

9. The method as claimed in claim 1, comprising:

providing a parameter service by the magnetic resonance facility via the interface, and with said parameter service providing the external control device with an interface in order to acquire parameter information that relates to parameters of sequences in the magnetic resonance facility.

10. The method as claimed in claim 9, comprising:

depending on a specific sequence, providing the external control device, by the magnetic resonance facility, with a subset of the parameters, and including in the subset parameters in the specific sequence that may be changed by the external control device with respect to the specific sequence.

11. The method as claimed in claim 9, comprising:

formulating the parameter information to include at least one item of information from an information set that includes the following information: an item of information on the availability and modifiability of the parameter, a designation of the parameter, a type and a unit for the parameter, valid values for the parameter, an item of information on a selectable value range for the parameter, a detailed description of the parameter, a clear identification of the parameter.

12. The method as claimed in claim 9, comprising:

at the external control device, generating or changing a subset of the parameters, said subset including said parameters in a sequence that can be changed by the external control device with respect to said sequence.

13. The method as claimed in claim 1, comprising:

establishing the communications link with acquisition of authorization data from the external control device, the authorization data comprising a license that states which services or instructions in the magnetic resonance facility can be carried out by the external control device;

carrying out the instruction acquired by the magnetic resonance facility depending on an authorization that is defined by the license; and dependent on said authorization data, defining the parameters that can be changed by said external control device.

14. A magnetic resonance facility comprising:

a magnetic resonance data acquisition scanner that is an operational state;

said magnetic resonance facility having an interface for communication with an external control device;

said magnetic resonance facility being configured to establish a communications link between the external control device and the magnetic resonance facility via the interface, with acquisition of authorization data from the external control device, the authorization data comprising a license that states which services or instructions in the magnetic resonance facility can be carried out by the external control device, and said authorization data changing said operational state to a license-defined state that permits its only said services or instructions stated in said license to be executed by said magnetic resonance facility;

said magnetic resonance facility being configured to acquire an instruction from the external control device via the interface;

said magnetic resonance facility being configured to carry out the instruction at the magnetic resonance facility in order to operate said magnetic resonance facility to acquire magnetic resonance data from a subject only when said instruction is permitted by the license comprised in said authorization data, with the acquired magnetic resonance data thereby being defined by said instruction; and said magnetic facility being configured to reconstruct an image of the subject from the acquired magnetic resonance data that were defined by said instruction, and to make the reconstructed image available in electronic form, as a data file.

15. A non-transitory, computer-readable data storage medium encoded with programming instructions, said storage medium being loaded into a computer system of a magnetic resonance facility, that is an operational state, and said programming instructions causing said computer system to:

establish a communications link between an external control device and an interface of the magnetic resonance facility;

at the magnetic resonance facility, acquire an instruction from the external control device via the interface, with acquisition of authorization data from the external control device, the authorization data comprising a license that states which services or instructions in the magnetic resonance facility can be carried out by the external control device, and said authorization data changing said operational state to a license-defined state that permits its only said services or instructions stated in said license to be executed by said magnetic resonance facility;

carry out the instruction at the magnetic resonance facility in order to operate said magnetic resonance facility to acquire magnetic resonance data from a subject only when said instruction is permitted by the license comprised in said authorization data, with the acquired magnetic resonance data thereby being defined by said instruction; and reconstruct an image of the subject from the acquired magnetic resonance data that were defined by said instruction, and make the reconstructed image available in electronic form, as a data file.

16. An imaging system comprising:

a magnetic resonance facility that is an operational state;

a control device that is external of said magnetic resonance facility;

said magnetic resonance facility having an interface for communication with the external control device;

said magnetic resonance facility being configured to establish a communications link between the external control device and the magnetic resonance facility via the interface, with acquisition of authorization data from the external control device, the authorization data comprising a license that states which services or instructions in the magnetic resonance facility can be carried out by the external control device, and said authorization data changing said operational state to a license-defined state that permits its only said services or instructions stated in said license to be executed by said magnetic resonance facility;

said magnetic resonance facility being configured to acquire an instruction from the external control device via the interface;

said magnetic resonance facility being configured to carry out the instruction at the magnetic resonance facility in order to operate said magnetic resonance facility to acquire magnetic resonance data from a subject only when said instruction is permitted by the license comprised in said authorization data, with the acquired magnetic resonance data thereby being defined by said instruction; and said magnetic facility being configured to reconstruct an image of the subject from the acquired magnetic resonance data that were defined by said instruction, and to make the reconstructed image available in electronic form, as a data file.

* * * * *